United States Patent
Chen

(10) Patent No.: US 9,687,694 B2
(45) Date of Patent: Jun. 27, 2017

(54) WEARABLE MUSCLE STRENGTH TRAINING DETECTOR DEVICE

(71) Applicant: BION INC., New Taipei (TW)

(72) Inventor: Yu-Yu Chen, Taipei (TW)

(73) Assignee: Bion Inc., New Taipei (TW)

( * ) Notice: Subject to any disclaimer, the term of this patent is extended or adjusted under 35 U.S.C. 154(b) by 356 days.

(21) Appl. No.: 14/460,497

(22) Filed: Aug. 15, 2014

(65) Prior Publication Data

US 2015/0057576 A1  Feb. 26, 2015

(30) Foreign Application Priority Data

Aug. 23, 2013 (TW) .............................. 102215831 U

(51) Int. Cl.
*A63B 24/00* (2006.01)
*A61B 5/00* (2006.01)
*A61B 5/22* (2006.01)

(52) U.S. Cl.
CPC ........ *A63B 24/0062* (2013.01); *A61B 5/0024* (2013.01); *A61B 5/224* (2013.01); *A61B 5/6824* (2013.01); *A61B 5/6828* (2013.01); *A61B 5/6829* (2013.01); *A61B 2562/08* (2013.01)

(58) Field of Classification Search
CPC ... A63B 24/0062; A61B 5/0024; A61B 5/224; A61B 5/6824; A61B 5/6828; A61B 5/6829; A61B 2562/08
See application file for complete search history.

(56) References Cited

U.S. PATENT DOCUMENTS

| | | | | |
|---|---|---|---|---|
| 5,857,939 A * | 1/1999 | Kaufman | ............... | A63B 24/00 482/1 |
| 6,014,078 A * | 1/2000 | Rojas | ................... | A63B 21/072 340/323 R |
| 7,232,416 B2* | 6/2007 | Czernicki | .............. | A61B 7/006 482/6 |
| 2002/0086774 A1* | 7/2002 | Warner | .............. | A63B 24/0021 482/8 |
| 2003/0163287 A1* | 8/2003 | Vock | .................... | A43B 3/0005 702/187 |
| 2007/0135264 A1* | 6/2007 | Rosenberg | ......... | A63B 24/0006 482/8 |
| 2007/0173377 A1* | 7/2007 | Jamsen | ................ | A61B 5/1123 482/8 |
| 2007/0232453 A1* | 10/2007 | Hanoun | ............... | A63B 21/225 482/7 |

(Continued)

*Primary Examiner* — Sundhara Ganesan
(74) *Attorney, Agent, or Firm* — Rosenberg, Klein & Lee

(57) ABSTRACT

A wearable muscle strength training detector device includes a sensor, a sensitivity adjustor, a data storage device, an identification code recognition unit, a display device, and a data input/output port. The sensitivity adjustor allows for adjustment to a desired sensitivity according to a selected body portion of the user. A wireless transceiver makes instantaneous transmission of muscle strength training data to a display device or transmission of the dynamic exercise signal from a data storage device to a central monitor and control unit. A plurality of peripheral detector devices are further provided to work with different types of muscle strength training device and is wearable on corresponding portions of the user to be wirelessly connected to a wearable muscle strength training detector device and displayed.

17 Claims, 7 Drawing Sheets

(56) References Cited

U.S. PATENT DOCUMENTS

| | | | |
|---|---|---|---|
| 2010/0259407 A1* | 10/2010 | Tilvis | A63B 24/0062 340/686.6 |
| 2011/0152045 A1* | 6/2011 | Horne | A63B 24/0062 482/131 |
| 2012/0184823 A1* | 7/2012 | Chen | A61B 5/0205 600/301 |
| 2012/0220429 A1* | 8/2012 | Yoshida | A63B 71/0686 482/8 |
| 2013/0072353 A1* | 3/2013 | Alessandri | A63B 21/062 482/8 |
| 2013/0171599 A1* | 7/2013 | Bleich | A61B 5/0456 434/247 |
| 2013/0190903 A1* | 7/2013 | Balakrishnan | A61B 5/7246 700/91 |

* cited by examiner

WEARABLE MUSCLE STRENGTH TRAINING DETECTOR DEVICE

BACKGROUND OF THE INVENTION

1. Field of the Invention

The present invention relates to a muscle strength training detector device, and in particular to a wearable muscle strength training detector device, which is body borne, allowing a user to wear on a wrist, a waist, or other suitable locations according to different types of muscle strength training device involved.

2. The Related Arts

A conventional muscle strength training device is provided for training of muscles of various parts of a human body and various models are available in the market. Due to the difference among muscles of various parts of a human body in respect of exercise mode and characteristics and also due to the significant diversification of physic conditions among different people, the muscle strength training must be achieved on the basis of the characteristics of the muscles of different parts. If a trainee is not guided by a trainer or a therapist or if his or her body has been hurt by sports injury or suffers other illness, the stretching force, weight, direction, posture, and the likes of training must be specifically adjusted, otherwise the training may be just in vain or may even cause sports injury, such as muscle straining.

A conventional way of measurement of muscle strength training is to provide detection devices, such as reed switches and laser sensors, which may be different to be mounted to different muscle strength training devices. With the increasingly progress of the development of the muscle strength training devices, they are getting more and more complicated and different sensor devices are provided for different parts of human body. This makes assembly hard and maintenance and repair are also difficult. In addition, such sensors for muscle strength training device must be combined with an wheel axle of a muscle strength training device. Manufacturers have to make multiple models of sensors to cope with the muscle strength training devices available in the market and this makes the manufacture hard.

Further, the conventional muscle strength training devices do not allow for regulation and adjustment made according to personal conditions and thus large error often results. This is also a shortcoming of the conventional detection devices.

SUMMARY OF THE INVENTION

In view of the shortcomings of the conventional devices, an object of the present invention is to provide, based on the difference of personal physiologic and physical conditions of users, a wearable muscle strength training detector device, which is personally bearable by a user to be worn on various parts, such as a wrist, an arm, the waist, and a foot.

The present invention allows for advance sensitivity adjustment in respect of a body portion of a user before muscle training is performed in order to achieve the best sensitivity of detection, instead of making adjustment based on the muscle strength training device used. Further, the present invention is applicable to all sorts of muscle strength training device available in the market. When the user is using a different muscle strength training device, it only needs to make adjustment of the wearable muscle strength training detector device of the present invention to achieve conversion.

To achieve the above object, the present invention provides a detector device that comprises a sensor, a sensitivity adjustor, a data storage device, an identification code recognition unit, a display device, and a data input/output port. The sensor is worn and fixed on a wrist of a user to make instantaneously measurement and detection of a dynamic exercise signal of the selected body portion. The sensitivity adjustor allows for adjustment to a desired sensitivity according to the selected portion of the user where the sensor is worn. The identification code identifies the type of the muscle strength training device used. In one embodiment, the present invention further comprises a wireless transceiver, which instantaneously transmits muscle strength training data to a display device of the muscle strength training device or transmits data stored in a data storage device to a central monitor and control unit.

In another embodiment, a plurality of peripheral detector devices is provided for working with different types of muscle strength training device and being wearable on corresponding body portions of the user, such as an arm, a leg, and afoot, to be connectable, in a wireless manner, to the wearable muscle strength training detector device, allowing the training data to be displayed on the display device of the wearable muscle strength training detector device.

BRIEF DESCRIPTION OF THE DRAWINGS

The present invention will be apparent to those skilled in the art by reading the following description of preferred embodiments of the present invention, with reference to the attached drawings, in which.

DETAILED DESCRIPTION OF THE PREFERRED EMBODIMENTS

Figure 1:
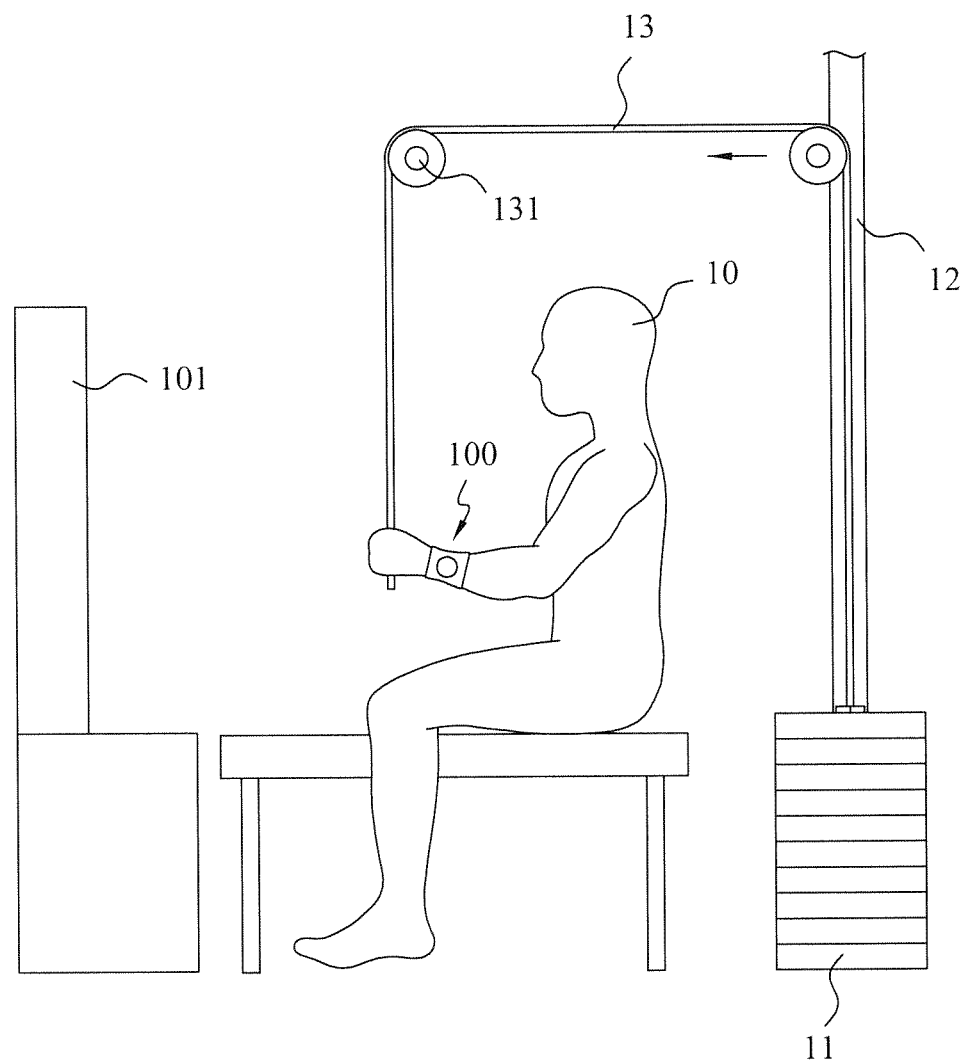
FIG. 1 is a schematic view showing a first embodiment according to the present invention.

With reference to the drawings and in particular to FIG. 1, which provides a schematic view of a wearable muscle strength training detector device 100 according to a first embodiment of the present invention, a user 10, who attempts to use a muscle strength training device to do muscle strength training, is shown wearing and fixing the wearable muscle strength training detector device 100 of the present invention on a wrist of the user 10 for instantaneous measurement and display of a dynamic exercise signal S1 of the human body portion and a muscle strength training display device 101 is provided to display the dynamic exercise signal SI for easy viewing by the user. The embodiment illustrated in the drawing gives an illustrative example that the user wears and fixes the wearable muscle strength training detector device 100 on the wrist to take muscle strength training with the muscle strength training device 1. The muscle strength training device 1 comprises at least one weight 11, at least one pair of support bars 12, a pull cord 13 connected to the weight 11, and one pair of pulley assemblies 131. The pull cord 13 is attached to the pulley assemblies 131 to allow the user to pull downward and once pulled, moves the weight 11 of the muscle strength training device 1 to achieve training. Further, the wearable muscle strength training detector device 100 of the present invention that is worn on the wrist of the user measures the condition of training of the user.

Figure 2:
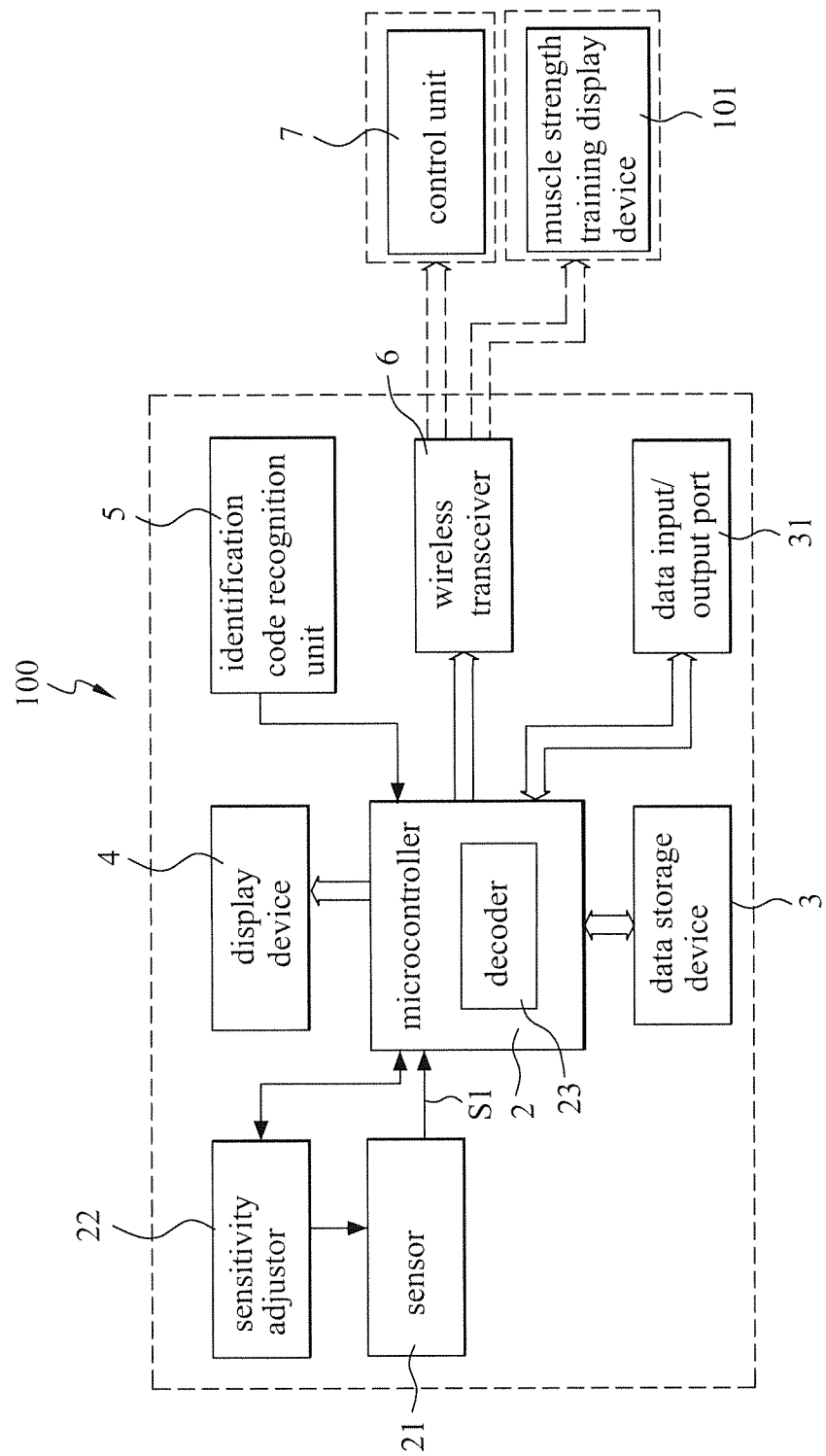
FIG. 2 is a circuit diagram of the first embodiment of the present invention.

Referring to FIG. 2, a circuit diagram of the first embodiment of the present invention is given and comprises: at least one microcontroller 2, at least one sensor 21, and a sensitivity adjustor 22. The sensor 21 is worn and fixed on a selected body portion of the user 10, such as a wrist, an arm, and a foot. The sensor 21 performs instantaneous measurement of the dynamic exercise signal S1 of the selected body portion. The sensor is connected to the microcontroller 2. Further, the sensitivity adjustor 22 is provided and connected with the sensor 21 and the microcontroller 2. The sensitivity adjustor 22 is provided for adjustment of the sensitivity of detection of the sensor 21 according to the selected portion of the user 10 on which the sensor is worn. The microcontroller 2 may include a decoder 23.

The wearable muscle strength training detector device 100 according to the present invention further comprises a data storage device 3 and a display device 4. The data storage device 3 stores the dynamic exercise signal S1 measured and detected by the sensor 21 and comprises a data input/output port 31 for input and output of at least one dynamic exercise signal S1.

As shown in the drawing, the wearable muscle strength training detector device 100 of the present invention comprises an identification code recognition unit 5, which is connected to the microcontroller 2. The identification code recognition unit 5 is provided for the purposes of handling the situation that muscle strength training devices available in the market include various types including for example a push type muscle strength training device, a pull type muscle strength training device, an arm swing type muscle strength training device, a foot press type muscle strength training device, a foot lifting type muscle strength training device, and other types of muscle strength training device, which provide different exercise modes of different human body portions and thus issue different signals to be received by the sensor 21. The identification code recognition unit 5 allows for recognition of the mode or type of the muscle strength training device that is to be used by the user 10 in order to automatically adjust the sensitivity adjustor 22.

According to the first embodiment of the present invention, a wireless transceiver 6 is further provided for transmitting instantaneous data, in a wireless manner, to the display device 4 and the muscle strength training display device 101 of the muscle strength training device or for transmitting the dynamic exercise signal S1 stored in the data storage device 3, through a wireless network, to a central monitor and control unit 7.

Figure 3:
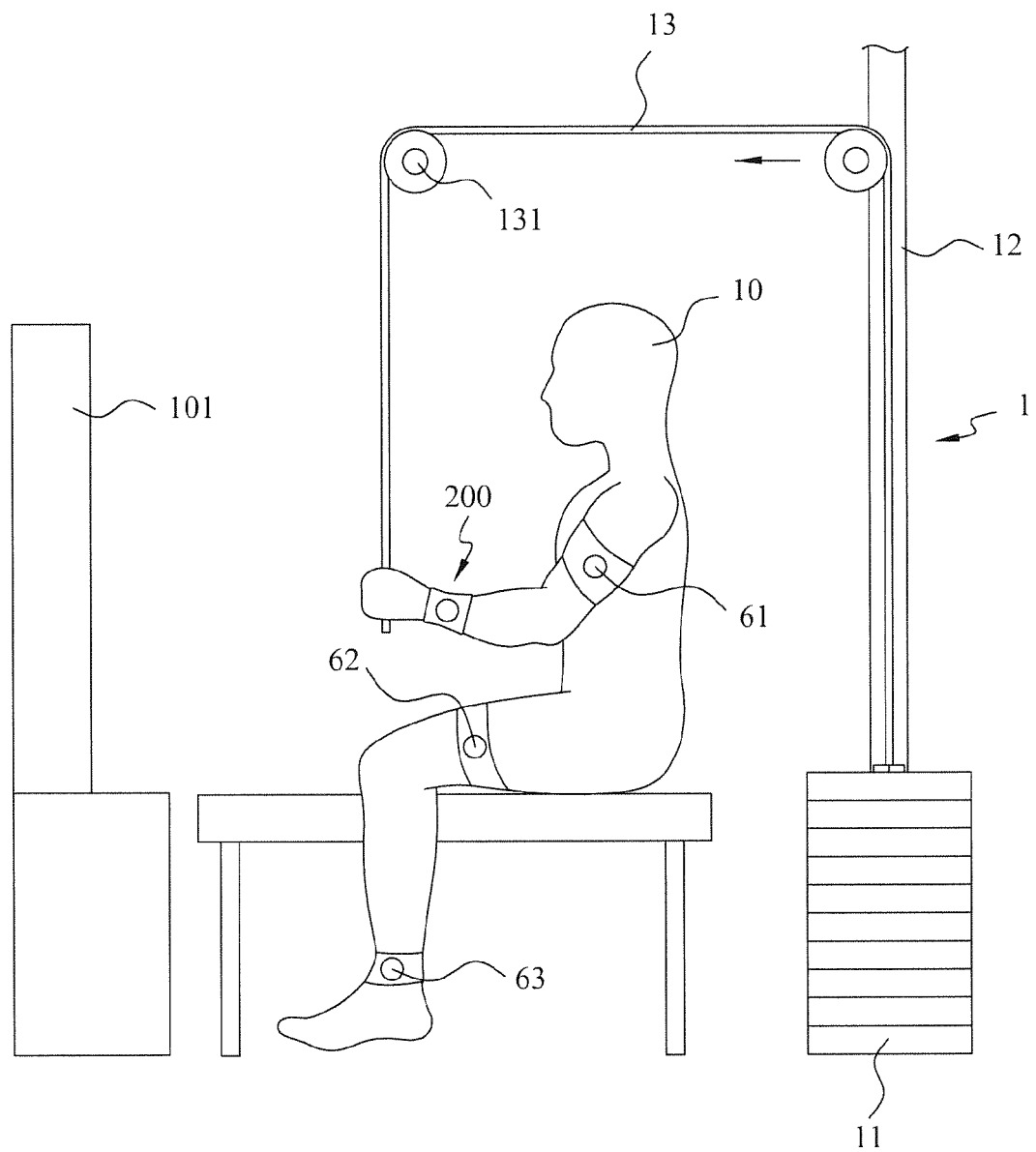
FIG. 3 is a schematic view showing a second embodiment according to the present invention.

Since in a gym or a similar place, there is often a plurality of muscle strength training devices installed and since a user 10 may use different ones of the muscle strength training devices by turns. To suit the need of the market, a wearable muscle strength training detector device 200 is provided according to a second embodiment of the present invention, which, as well as a third embodiment that will be described later, is substantially similar to the first embodiment described previously, so that similar parts/components will bear the same reference numerals for consistency. In the second embodiment, a plurality of peripheral detector devices 61, 62, 63 (see FIGS. 3 and 4) is provided. The peripheral detector devices 61, 62, 63 are workable with different types or modes of muscle strength training device and are wearable on corresponding body portions of the user that are subjected to training, such as an arm, a leg, and a foot, and a wireless transceiver 6a is provided for transmitting, in a wireless manner, a plurality of dynamic exercise signals S21、S22、S23 detected by the peripheral detector devices 61, 62, 63 to the wearable muscle strength training detector device 200. The microcontroller 2 is capable of distinguishing different dynamic exercise signals transmitted from the peripheral detector devices 61, 62, 63 by means of the decoder 23.

Figure 5:
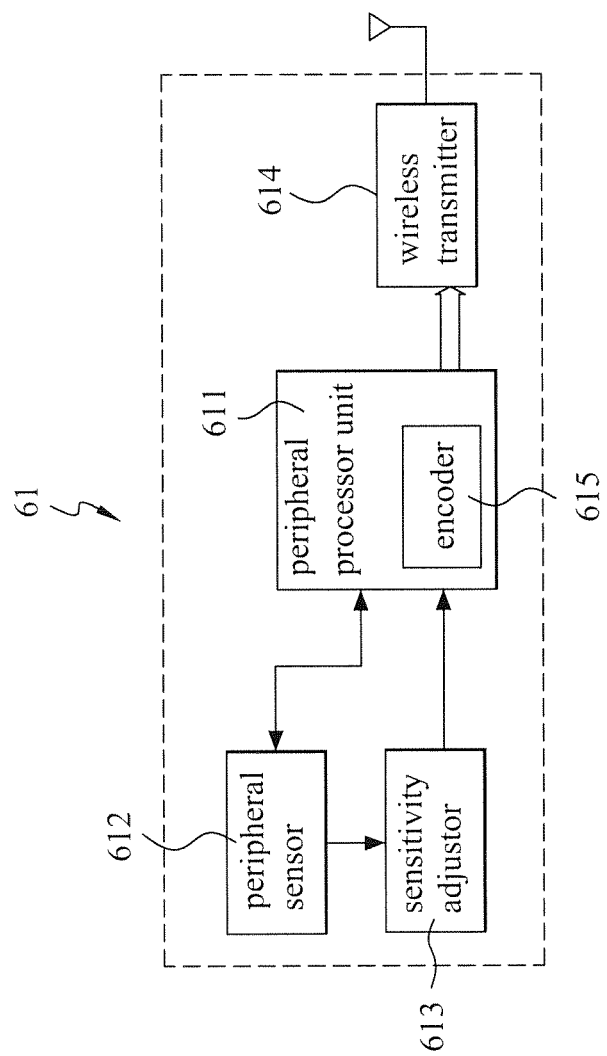
FIG. 5 is a circuit diagram of a peripheral detector device according to the second embodiment of the present invention.

Referring to FIG. 5, taking the peripheral detector device 61 as an example, the peripheral detector devices 61 comprises a peripheral processor unit 611, a peripheral sensor 612, a sensitivity adjustor 613, and a wireless transmitter 614. The peripheral processor unit 611 includes an encoder 615 capable of providing an identification code to the peripheral detector device 61.

Figure 4:
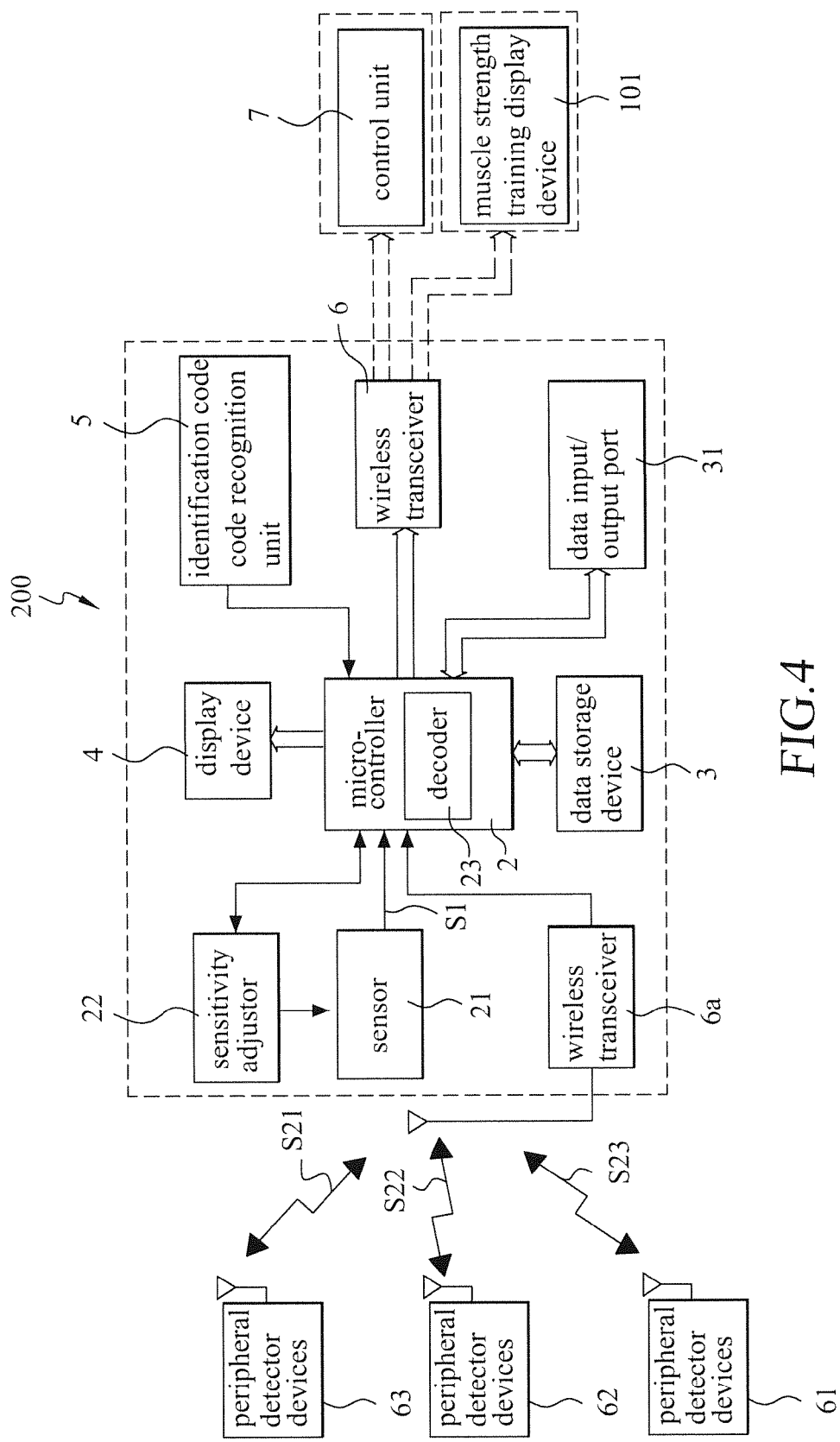
FIG. 4 is a circuit diagram of the second embodiment of the present invention.

Similar to the counterpart of the first embodiment, the wearable muscle strength training detector device 200 is worn on the wrist of the user to receive, in a wireless manner, data transmitted from the peripheral detector device 61 (as shown in FIG. 4), to similarly allow the user to view the result of training through the display device 4 and the muscle strength training display device 101 of the wearable muscle strength training detector device 200.

Figure 6:
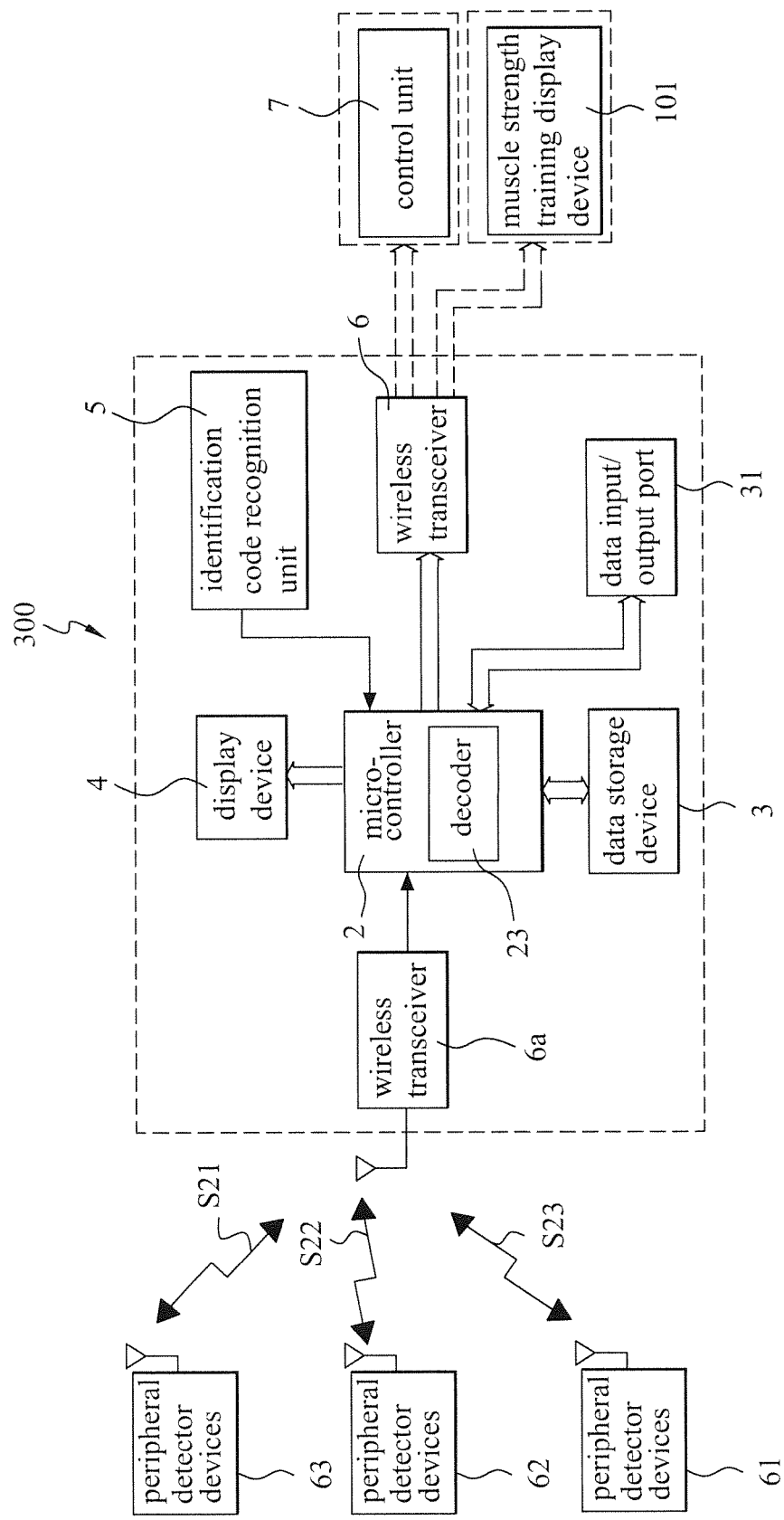
FIG. 6 is a circuit diagram of the second embodiment of the present invention.

Referring to FIG. 6, a circuit diagram of the third embodiment of present invention is shown. The instant embodiment is similar to the second embodiment; however a wearable muscle strength training detector device 300 of the instant embodiment is structured with the sensor 21 and the sensitivity adjustor 22 removed and omitted so that the wearable muscle strength training detector device of the instant embodiment does not possess the capability of detection and adjustment and cannot work alone and must be set in connection with the peripheral detector device 61, 62, 63 in such a way that detection is achieved with the peripheral detector devices 61, 62, 63. A wireless transceiver 6a is provided for transmitting, in a wireless manner, a plurality of dynamic exercise signals S21、S22、S23 detected by the peripheral detector devices 61, 62, 63 to the wearable muscle strength training detector device 300.

Figure 7:
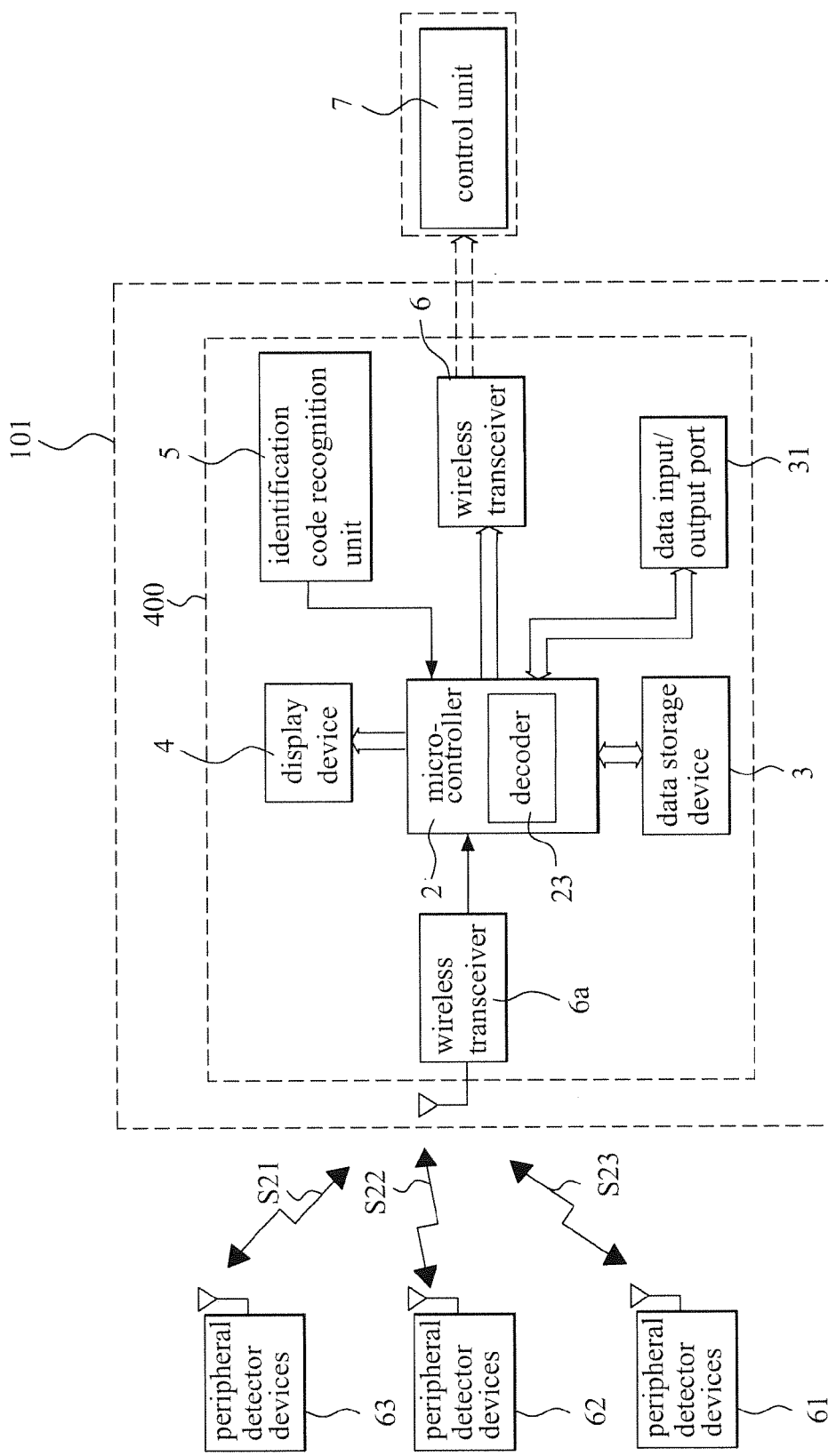
FIG. 7 is a circuit diagram of the second embodiment of the present invention.

Referring to FIG. 7, a circuit diagram of a fourth embodiment of present invention is shown. The instant embodiment is structured in a way similar to the third embodiment; however the wearable muscle strength training detector device 400 of the instant embodiment is integrated in the muscle strength training display device 101 configured for the muscle strength training device 1 and each of the peripheral detector devices 61, 62, 63 is worn and fixed on a selected peripheral portion of the user.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. A wearable muscle strength training detector device electrically connectable to a muscle strength training device, the wearable muscle strength training detector device being configurable for wear on a selected portion of a user's body, the wearable muscle strength training detector device comprising:

a microcontroller;

at least one sensor connected to the microcontroller to instantaneously detect a dynamic exercise signal generated responsive to movement of the selected portion of the user's body;

an identification code recognition unit connected to the microcontroller to recognize a type of the muscle strength training device used; and at least one sensitivity adjustor connected to the sensor and the microcontroller, the sensitivity adjustor selectively setting a desired sensitivity according to the selected portion of the user's body on which the sensor is worn and responsively adjusting the sensitivity according to the type of the muscle strength training device recognized by the identification code recognition unit.

2. The wearable muscle strength training detector device as claimed in claim 1 further comprising a data storage device to store the dynamic exercise signal.

3. The wearable muscle strength training detector device as claimed in claim 1 further comprising a display device to display the dynamic exercise signal.

4. The wearable muscle strength training detector device as claimed in claim 1, wherein the type of the muscle strength training device is one of a push type muscle strength training device, a pull type muscle strength training device, an arm swing type muscle strength training device, a foot press type muscle strength training device, a foot lifting type muscle strength training device, and other muscle strength training devices.

5. The wearable muscle strength training detector device as claimed in claim 1 further comprising a data input/output port for input and output of the dynamic exercise signal.

6. The wearable muscle strength training detector device as claimed in claim 1, wherein the dynamic exercise signal is transmitted through a wireless transceiver to a central monitor and control unit in a wireless manner.

7. The wearable muscle strength training detector device as claimed in claim 1, wherein the dynamic exercise signal is transmitted through a wireless transceiver to a muscle strength training display device of the muscle strength training device in a wireless manner.

8. The wearable muscle strength training detector device as claimed in claim 1 further comprising:

at least one peripheral detector device worn and fixed on a selected peripheral portion of the user to instantaneously detect the dynamic exercise signal of the selected peripheral portion of the user, the peripheral detector device comprising:

a peripheral processor unit;

at least one peripheral sensor connected to the peripheral processor unit to instantaneously detect the dynamic exercise signal;

at least one sensitivity adjustor connected to the peripheral sensor and the peripheral processor unit to set a desired sensitivity according to the selected peripheral portion of the user on which the peripheral sensor is worn; and a wireless transceiver connected to the peripheral processor unit to receive the dynamic exercise signal detected by the peripheral sensor of the peripheral detector device.

9. A wearable muscle strength training detector device electrically connectable to a muscle strength training device, the wearable muscle strength training detector device being configurable for wear on a selected portion of a user's body, the wearable muscle strength training detector device comprising:

a microcontroller;

an identification code recognition unit connected to the microcontroller to recognize a type of the muscle strength training device used; and at least one peripheral detector device worn and fixed on a selected peripheral portion of the user's body to instantaneously detect a dynamic exercise signal generated responsive to movement of the selected peripheral portion of the user's body, the peripheral detector device comprising:

a peripheral processor unit, at least one peripheral sensor which connected to the peripheral processor unit to instantaneously detect the dynamic exercise signal generated responsive to movement of the selected portion of the user's body, at least one sensitivity adjustor connected to the peripheral sensor and the peripheral processor unit, the sensitivity adjustor selectively setting a desired sensitivity according to the selected peripheral portion of the user's body on which the peripheral sensor is worn and responsively adjusting the sensitivity according to the type of the muscle strength training device recognized by the identification code recognition unit, and a wireless transceiver, which is connected to the peripheral processor unit to receive the dynamic exercise signal detected by the peripheral sensor of the peripheral detector device.

10. The wearable muscle strength training detector device as claimed in claim 9 further comprising a data storage device to store the dynamic exercise signal.

11. The wearable muscle strength training detector device as claimed in claim 9 further comprising a display device to display the dynamic exercise signal.

12. The wearable muscle strength training detector device as claimed in claim 9, wherein the type of the muscle strength training device is one of a push type muscle strength training device, a pull type muscle strength training device, an arm swing type muscle strength training device, a foot press type muscle strength training device, a foot lifting type muscle strength training device, and other muscle strength training devices.

13. The wearable muscle strength training detector device as claimed in claim 9 further comprising a data input/output port for input and output of the dynamic exercise signal.

14. The wearable muscle strength training detector device as claimed in claim 9, wherein the dynamic exercise signal is transmitted through a wireless transceiver to a central monitor and control unit in a wireless manner.

15. The wearable muscle strength training detector device as claimed in claim 9, wherein the dynamic exercise signal is transmitted through a wireless transceiver to a muscle strength training display device of the muscle strength training device in a wireless manner.

16. The wearable muscle strength training detector device as claimed in claim 9 mounted in a muscle strength training display device of the muscle strength training device, each of the peripheral detector devices being worn and fixed on a selected peripheral portion of the user.

17. The wearable muscle strength training detector device as claimed in claim 9, comprising a plurality of the peripheral detector devices, wherein the peripheral processor unit of each of the peripheral detector devices includes an encoder for establishing a peripheral detector device identification code; and, the microcontroller includes a decoder for processing the peripheral detector device identification code of each of the peripheral detector devices.

* * * * *